United States Patent [19]

Lary

[11] Patent Number: 5,556,405
[45] Date of Patent: Sep. 17, 1996

[54] UNIVERSAL DILATOR WITH RECIPROCAL INCISOR

[75] Inventor: Banning G. Lary, Miami, Fla.

[73] Assignee: Interventional Technologies Inc., San Diego, Calif.

[21] Appl. No.: 543,091

[22] Filed: Oct. 13, 1995

[51] Int. Cl.⁶ .................................................... A61B 17/22
[52] U.S. Cl. ................................... 606/159; 606/171
[58] Field of Search .................................. 606/159, 171, 606/160

[56] References Cited

U.S. PATENT DOCUMENTS

| | | |
|---|---|---|
| 2,505,358 | 4/1950 | Gusberg et al. . |
| 2,749,909 | 9/1954 | Ullery et al. . |
| 4,273,128 | 6/1981 | Lary . |
| 4,723,549 | 2/1988 | Wholey et al. . |
| 4,966,604 | 10/1990 | Reiss ........................................ 606/159 |
| 5,053,044 | 10/1991 | Mueller et al. . |
| 5,192,291 | 3/1993 | Pannek, Jr. ............................... 606/159 |
| 5,224,945 | 7/1993 | Pannek, Jr. ............................... 606/159 |
| 5,224,949 | 7/1993 | Gomringer et al. . |
| 5,372,601 | 12/1994 | Lary ........................................ 606/159 |

FOREIGN PATENT DOCUMENTS

| | | |
|---|---|---|
| 3231127 | 2/1984 | Germany . |
| 3519626 | 12/1986 | Germany . |
| 3732236 | 12/1988 | Germany . |
| 1516120 | 10/1989 | U.S.S.R. . |

OTHER PUBLICATIONS

Banning G. Lary, MD, *Coronary Artery Incision and Dilation,* Archives of Surgery, Dec. 1980, vol. 115.
Banning G. Lary, M.D., *Onlay Vein Graft for the Correction of Coronary Artery Obstruction,* Surgery, Apr. 1966, vol. 59, No. 4, pp. 547–551.

*Primary Examiner*—Michael Powell Buiz
*Assistant Examiner*—Kevin Truong
*Attorney, Agent, or Firm*—Nydegger & Associates

[57] ABSTRACT

A device for incising and dilating a stenosis in a vessel of a patient includes a dilator housing and a plurality of incising blades which can be selectively extended distally from the housing. Specifically, the plurality of blades are mounted on a base member which is attached to the distal end of a push-pull catheter. The housing has a plurality of slits which are positioned distally from the base member with the blades on the base member in alignment with the slits in the housing. A placement catheter is positioned in a surrounding relationship over the push-pull catheter, and the distal end of the placement catheter is attached to the housing to create a chamber between the placement catheter and the housing in which the base member is located. In the operation of the device, the push-pull catheter is manipulated distally and proximally in the placement catheter to move the base member within the chamber between a first position and a second position. In the first position the blades are withdrawn into the housing and the housing is used as a dilator. In the second position the blades are extended distally through the slits in the housing and the device is used as an incisor.

18 Claims, 1 Drawing Sheet

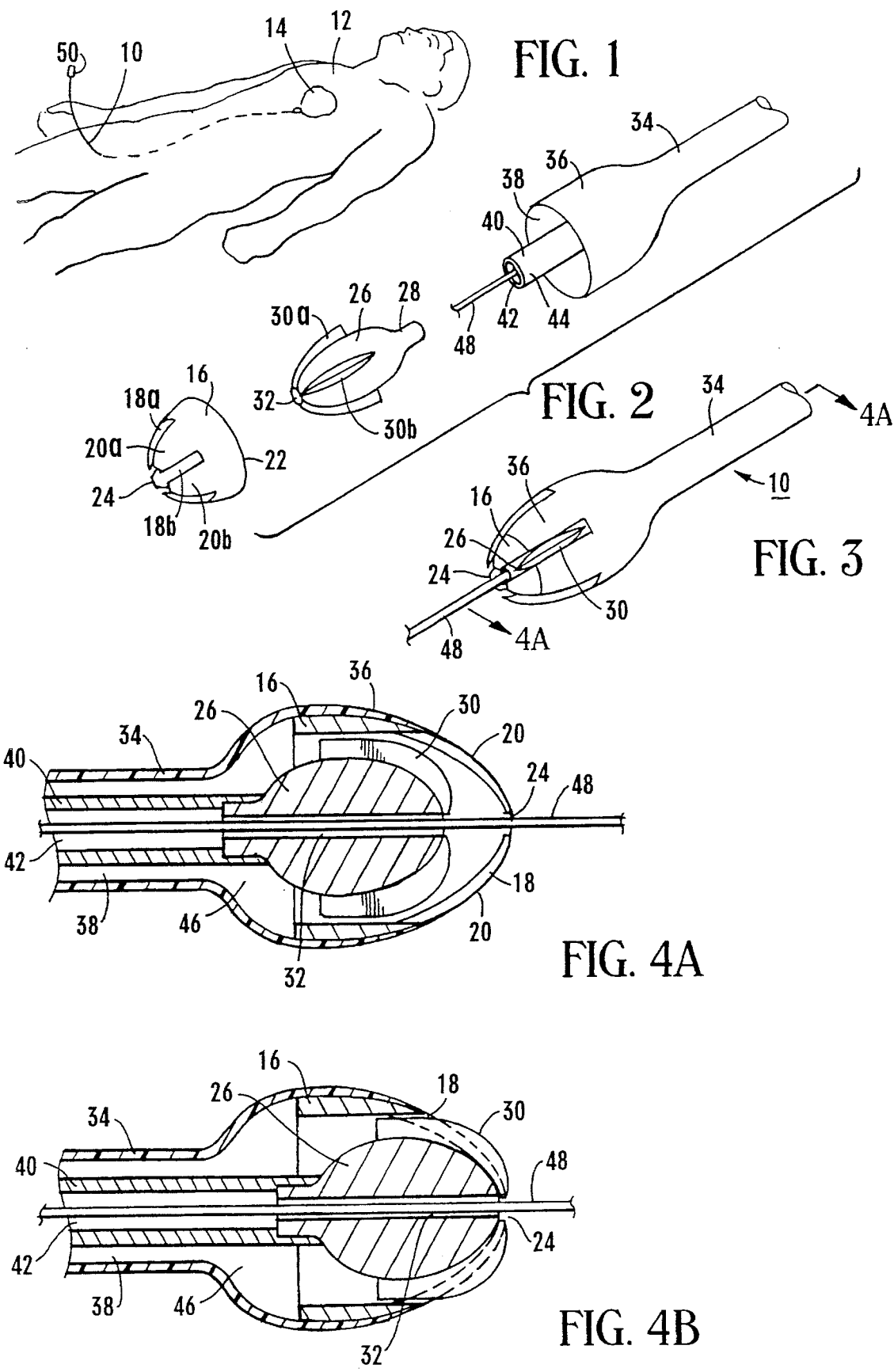

UNIVERSAL DILATOR WITH RECIPROCAL INCISOR

FIELD OF THE INVENTION

The present invention pertains generally to cardiovascular surgical tools. More particularly, the present invention pertains to surgical tools which are useful for clearing a stenosis from a vessel of a patient. The present invention is particularly, but not exclusively, useful as a mechanical dilator which can be selectively altered in its configuration to create incisions in a stenosis as the dilator is being distally advanced through the stenosis.

BACKGROUND OF THE INVENTION

Stenotic segments in the vessels and arteries of a patient can develop for many different reasons and can have different adverse effects on the patient. Depending on the location of the particular stenosis, the patient can experience cardiac arrest, stroke, or tissue and organ necrosis. Further, the severity of damage to the patient will, at least to some extent, depend on the nature of the stenosis and the extent of its development. Suffice it to say, stenotic segments can develop throughout a patient's cardio-vascular system, and can vary in size, shape and composition. Consequently, they vary in the degree to which they occlude blood flow through the vessel.

A stenosis in a vessel can be quite extensive and occlude a substantial length of a vessel. On the other hand, some stenoses are quite short. Further, some stenoses are highly calcified while other are not. The consequence is that, depending on the nature of the particular stenosis, some surgical tools and procedures are more appropriate than are others for clearing the stenosis.

Angioplasty is one of several types of medical procedures which has been widely used in recent years to surgically clear a stenosis in a vessel. More specifically, in an angioplasty procedure, a balloon is placed across the stenosis where it is inflated to dilate the stenosis.

Atherectomy is another type of medical procedure which, as an alternative to angioplasty, has been an acceptable and widely used procedure for surgically clearing a stenosis from a vessel. Quite unlike an angioplasty procedure, however, an atherectomy procedure results in the clearing of the vessel by cutting and removing the stenotic plaque from the vessel.

Still another type medical procedure, though somewhat like angioplasty in its effect on the stenosis, is a dilatation probe. For a procedure using a dilatation probe, the stenosis is simply approached by the probe and the probe is then pushed or urged through the stenosis. In an aggressive procedure, the probe can be moved back and forth through the stenosis. In any event, due to the dilating or spreading effect of the probe, the stenosis can be cleared. Further, in comparison with either an angioplasty or an atherectomy procedure, the use of a dilatation probe is relatively simple.

It has been determined that the dilatation of a stenosis is greatly facilitated if the stenosis is incised before the dilatation. Consequently, several devices have been proposed for this purpose. For example, U.S. Pat. No. 4,273,128 which issued to Lary for and invention entitled "Coronary Cutting and Dilating Instrument" discloses a serial combination of a distal longitudinal incisor and a proximal dilatation balloon. Further, U.S. Pat. No. 5,320,634 which issued to Vigil et al. for an invention entitled "Balloon Catheter with Seated Cutting Edges" discloses a device in which the incising blades are carried on the surface of the angioplasty balloon. Both of these patents are assigned to the same assignee as the present invention.

There is, of course, an ever present danger when sharp instruments are inserted into and through a vessel of a patient to incise tissue. Very importantly, the incising instrument, i.e. a sharpened blade, needs to be effectively covered during its insertion into the vessel in order to protect the vessel from inadvertent incisions. Such protection becomes increasingly more important as the distance for travel of the incising instrument through the vessel increases.

In light of the above, it is an object of the present invention to provide a universal incisor/dilator surgical tool which can selectively extend blades from the tool for incision of a stenotic segment. Another object of the present invention is to provide a universal incisor/dilator surgical tool which keeps its incising blades covered, to protect against inadvertent incision of the vessel wall, during transit of the tool through an artery or vessel to the stenosis. Yet another object of the present invention is to provide a surgical tool which can act simply as a dilator or, alternatively, as an incisor. Still another object of the present invention is to provide a universal incisor/dilator surgical tool which is relatively easy to manufacture, is simple to operate and is comparatively cost effective.

SUMMARY OF THE INVENTION

In accordance with the present invention, a device for incising and dilating a stenosis in a vessel of a patient includes both a dilator housing and incising blades which are selectively extended from the dilator housing. More specifically, the dilator housing is shaped and dimensioned to dilate a stenosis in a vessel of a patient as it is either advanced or withdrawn through the stenosis. Additionally, the dilator housing is convertible into an incisor which includes a plurality of blades. To accomplish this conversion, the blades are moveable relative to the dilator housing to selectively extend them from the dilator housing. When so extended, the blades are used to incise the stenosis during a distal advancement of the dilator housing. Details of component structure for the device of the present invention are as follows. A base member in the device is formed with a plurality of elongated blades which extend outwardly from the base member. Preferably, both the base member and the blades are made of metal. A push-pull catheter, which is bendable but which also has good axial strength, has a distal end which is fixedly attached to the base member.

The device also has a hollow housing. The housing is generally cone shaped with a distally decreasing taper and has an open proximal end. The housing is preferably made of a rigid plastic, such as ABS, and is formed with a plurality of longitudinally oriented slits. A placement catheter, having a flared distal end, is fixedly attached to the open base end of the housing to create a chamber between the housing and the distal end of the placement catheter.

To construct the device of the present invention, the base member is positioned into the flared distal end of the placement catheter, and the push-pull catheter is inserted through the lumen of the placement catheter for attachment to the base member. The housing is then placed over the base member and attached to the flared distal end of the placement catheter. The base member is thus positioned in the chamber that is formed between the housing and the distal end of the placement catheter. Further, the blades on the base member are aligned with the slits in the housing. With this construction, the push-pull catheter is able to move the base member relative to the placement catheter and housing to extend the blades from the housing.

In the operation of the device of the present invention, the push-pull catheter is manipulated to selectively move the base member in the chamber between a first position and a second position. In the first position, the base member and attached blades are withdrawn proximally into the chamber to configure the device as a dilator. With the device configured as a dilator, no blades extend from the housing and the cone shaped housing can be moved distally and proximally through a stenosis in a vessel to dilate the stenosis. On the other hand, when the base member is moved distally into the second position by the push-pull catheter, the blades extend from the housing through the slits. This configures the device as an incisor. With the incisor configuration, a distal advancement of the device will cause the blades to make incisions into the stenosis to facilitate subsequent dilatation of the stenosis. As is to be appreciated, the housing will act as a dilator when the blades are extended therefrom, as well as when the blades are withdrawn into the housing.

BRIEF DESCRIPTION OF THE DRAWINGS

The novel features of this invention, as well as the invention itself, both as to its structure and its operation will be best understood from the accompanying drawings, taken in conjunction with the accompanying description, in which similar reference characters refer to similar parts, and in which:

FIG. 1 is a view of a patient and the intended environment for operation of the universal incisor/dilator of the present invention;

FIG. 2 is an exploded perspective view of the operative components of the present invention;

FIG. 3 is a perspective view of the present invention;

FIG. 4A is a cross sectional view of the present invention as seen along the line 4A—4A in FIG. 3, with the incisor blades in the first position wherein they are withdrawn into the housing; and FIG. 4B is a cross sectional view of the present invention as seen in FIG. 4a with the incisor blades in the second position wherein they are distally extended from the housing.

DESCRIPTION OF THE PREFERRED EMBODIMENTS

Referring initially to FIG. 1, the universal incisor/dilator device 10 of the present invention is shown inserted into the vessel of a patient 12. For purposes of illustration, the device 10 is shown in an operational position after being advanced through the femoral artery and toward the heart 14 of the patient 12. It is to be appreciated, however, that the device 10 is useful in vessels throughout the cardiovascular system of patient 12 and may be introduced into the vessel wherever it is most convenient to do so.

Referring now to FIG. 2, it will be seen that the device 10 of the present invention includes a housing 16. Specifically, the housing 16 is generally cone shaped and has a distally decreasing taper. Further, housing 16 is formed with a plurality of slots 18, of which the slots 18a and 18b are exemplary. As shown, the slots 18 are established between respective pairs of extensions 20, e.g. extensions 20a and 20b. As shown these are a plurality of extensions 20 which protrude from the distal end 22 of housing 16. At the distal end of housing 16, the extensions terminate to create a distal end opening 24. Preferably, housing 16 is made of a hard rigid plastic such as ABS.

FIG. 2 also shows that the device 10 includes a base member 26 which is formed with a projection 28. For the device 10, a plurality of blades 30 are mounted on base member 26. More specifically, the blades 30, of which blades 30a and 30b are exemplary, are oriented longitudinally on base member 26 and spaced thereon for alignment with a respective slit 18 in housing 16. It will be appreciated by the skilled artesan that blades 30 may be integrally formed with base member 26. Further, the base member 26 is formed with a lumen 32 which runs longitudinally through base member 26. Preferably, base member 26 and the blades 30 are made of a metal.

Device 10 further includes a placement catheter 34 which has a flared distal end 36 and a lumen 38 which extends the entire length of the placement catheter 34. Additionally, device 10 includes a push-pull catheter 40 which can be slidably received through the lumen 38 of placement catheter 34. As also shown in FIG. 2, the push-pull catheter 40 is formed with a lumen 42 which extends its entire length. Also, push-pull catheter 40 has a distal end 44.

For purposes of the present invention, placement catheter 34 should be somewhat flexible in order to permit advancement of the device 10 through a vessel of the patient 12. For the same reason, push-pull catheter 40 needs to be flexible. However, in addition to being flexible like the placement catheter 34, push-pull catheter 40 must have sufficient axial strength to facilitate movement of push-pull catheter 34 back and forth through lumen 38 of placement catheter 34.

In the manufacture of the device 10, the various components of device 10 are assembled into the combination shown in FIG. 3. To do this, the distal end 44 of push-pull catheter 40 is attached to projection 28 of base member 26 by any means well known in the pertinent art, such as by bonding. This attachment connects lumen 32 of base member 26 with lumen 42 of push-pull catheter to establish a contiguous lumen therethrough. Next, push-pull catheter 40 is inserted into lumen 38 of the placement catheter 34.

With base member 26 attached to push-pull lumen 42, the housing 16 is positioned adjacent base member 26. More specifically, the housing 16 is oriented on base member 26 so that the blades 30 of base member 26 are aligned with the slits 18 of housing 16. The flared end 36 of placement catheter 34 is then joined with the proximal end 22 of housing 16 by any means well known in the art, such as by solvent bonding.

The joinder of placement catheter 34 with housing 16 creates a chamber 46 which is best seen with reference to FIGS. 4A and 4B. Further, as best appreciated with reference to FIGS. 3, 4A or 4B, the flared distal end 36 of placement catheter 34 may, during initial construction of the device 10, cover portions of the slits 18. Should this occur, the material from catheter 34 which is covering slits 18 can be cut and removed to clear the slits 18.

The Figures also show that the device 10 can be used in cooperation with a guidewire 48. More specifically, the guidewire 48 can be of any type well known in the pertinent art which can be slidingly inserted through lumen 42 of push-pull catheter 40, lumen 32 of base member, and opening 24 of housing 16.

In the operation of the device 10, the guidewire 48 is first prepositioned in the vessel of patient 12 for the purpose of establishing a pathway to the stenotic segment (not shown)

which is to be dilated. The device 10 is then advanced over the guidewire 48 to position the housing 16 at the site of the stenotic segment. During the advancement of device 10 over guidewire 48, the device 10 is preferably configured with base member 26 is in its first position (shown in FIG. 4A). In this configuration the base member 26 is positioned proximally in chamber 46 and the blades 30 of base member 26 are thus withdrawn into the chamber 46.

Once the housing 16 of device 10 is positioned at the site of the stenotic segment, push-pull catheter 40 can be manipulated to move base member 26 from its first position (shown in FIG. 4A) to its second position (shown in FIG. 4B). In its second position, base member 26 is positioned distally in the chamber 46 and the blades 30 of base member 26 are extended distally from the housing 16 through slits 18. Consequently, any further movement of device 10 along guidewire 48 in the distal direction will cause blades 30 to incise the stenosis. This incision will then be immediately followed with a dilatation of the stenosis caused by the simultaneous distal advancement of housing 16. To facilitate this procedure, and to insure that base member 26 remains in its second configuration with blades 30 distally extended from device 10 during distal advancement of the device 10, the push-pull catheter 40 can be temporarily clamped to the placement catheter 34 by the clamp 50. Clamp 50 may be of any type well known in the art.

It is to be appreciated that, at the stenosis, device 10 can be manipulated back and forth in the distal and proximal directions through the vessel of patient 12 as desired by the user. Thus, incision and dilatation of the stenotic segment can be as aggressive as is required. Further, as deemed necessary, the blades 30 on base member can be selectively extended, to provide an incisor/dilator action during distal advance of the device 10, or retracted, to provide only a dilitation action.

While the particular universal incisor/dilator as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

We claim:

1. A device for incising and dilating a stenosis in a vessel which comprises:

a base member;

a plurality of blades mounted on said base member;

a housing formed with a plurality of slits;

a placement catheter, said placement catheter being formed with a lumen and having a distal end, said distal end of said placement catheter being attached to said housing to form a chamber therebetween, said base member being positioned in said chamber with said blades aligned with said slits; and a push-pull catheter inserted through said lumen of said placement catheter and attached to said base member for movement of said base member in said chamber between a first position wherein said blades are withdrawn into said housing for use of said device as a dilator and a second position wherein said blades extend through said slits of said housing for use of said device as an incisor.

2. A device as recited in claim 1 wherein said housing is substantially cone shaped with a distally decreasing taper.

3. A device as recited in claim 1 further comprising means for selectively fixedly holding said base member alternatively in said first position or in said second position.

4. A device as recited in claim 1 wherein said push-pull catheter and said base member are formed with a contiguous lumen and said device further comprises a guidewire insertable through said lumen, said guidewire being prepositionable in a vessel of a patient for advancing said device to a stenosis in the vessel.

5. A device as recited in claim 1 wherein said base member and said blades are made of a metal.

6. A device as recited in claim 1 wherein said housing is made of a rigid plastic.

7. A device as recited in claim 1 wherein said placement catheter is made of PET.

8. A device which comprises:

means for dilating a stenosis in a vessel of a patient;

means having a plurality of blades for incising the stenosis, said dilating means surrounding said incising means to create a chamber for said incising means, said incising means being moveable in said chamber between a first position wherein said blades are withdrawn into said chamber and a second position wherein said blades extend from said chamber and from said dilating means for incision of the stenosis; and means attached to said incising means for moving said incising means between said first position and said second position.

9. A device as recited in claim 8 wherein said dilating means comprises a housing formed with a plurality of slits and a placement catheter, said placement catheter being formed with a lumen and having a distal end attached to said housing to form said chamber.

10. A device as recited in claim 9 wherein said incising means is a base member positioned in said chamber, said blades being mounted on said base member and aligned with said slits in said housing.

11. A device as recited in claim 10 wherein said incising means further comprises a push-pull catheter inserted through said lumen of said placement catheter and attached to said base member for movement of said base member in said chamber between said first position and said second position.

12. A device as recited in claim 9 wherein said housing is substantially cone shaped with a distally decreasing taper.

13. A device as recited in claim 12 further comprising means for selectively fixedly holding said base member alternatively in said first position or in said second position.

14. A device as recited in claim 12 wherein said push-pull catheter and said base member are formed with a contiguous lumen and said device further comprises a guidewire insertable through said lumen, said guidewire being prepositionable in a vessel of a patient for advancing said device to a stenosis in the vessel.

15. A device as recited in claim 12 wherein said base member and said blades are made of a metal.

16. A device as recited in claim 12 wherein said housing is made of a rigid plastic.

17. A device as recited in claim 12 wherein said placement catheter is made of PET.

18. A method for manufacturing a device for incising and dilating a stenosis in a vessel of a patient which comprises the steps of:

mounting a plurality of blades on a base member;

positioning said base member adjacent a housing, said housing being formed with a plurality of slits, and said base member being positioned with said plurality of blades aligned with respective said slits;

attaching a push-pull catheter to said base member;

inserting said push-pull catheter through the lumen of a placement catheter for slidable movement therebetween; and attaching said placement catheter to said housing over said base member to create a chamber between said housing and said placement catheter, said base member being moveable in said chamber between a first position wherein said blades are withdrawn into said chamber and a second position wherein said blades extend from said chamber and from said housing for incising the stenosis.

* * * * *